United States Patent [19]

Kiefer

[11] Patent Number: 4,946,952

[45] Date of Patent: Aug. 7, 1990

[54] PROCESS FOR ISOLATING NUCLEIC ACIDS

[75] Inventor: Hansruedi Kiefer, Riehen, Switzerland

[73] Assignee: Hoffmann-La Roche Inc., Nutley, N.J.

[21] Appl. No.: 175,885

[22] Filed: Apr. 1, 1988

[30] Foreign Application Priority Data

Apr. 24, 1987 [CH] Switzerland ................................ 1573

[51] Int. Cl.$^5$ ...................... C07H 21/04; C07H 21/02; C07H 21/00
[52] U.S. Cl. ........................................ 536/27; 536/28; 536/29; 536/127
[58] Field of Search ........................ 536/22, 28, 29, 127

[56] References Cited

U.S. PATENT DOCUMENTS 3,597,318  8/1971  Sutherland et al. .................. 435/91

FOREIGN PATENT DOCUMENTS 1617498  2/1966  Fed. Rep. of Germany .
263036  11/1949  Switzerland .

OTHER PUBLICATIONS

Kochetkov et al., Organic Chemistry of Nucleic Acids, Part A, Plenum Press, New York, 1971, pp. 18–28.
Aonuma et al., Biol Abstr., 70(2): 11700, 1979.
Hellen et al., Biol. Abstr., 85(5):53654, 1987.
Imai, Chem. Abstr. 106:98488v, 1987.
Clark et al., Experimental Biochemistry, W. H. Freeman and Co., San Francisco, 1977, pp. 73–74.
Scopes, Protein Purifications, Springer-Verlag, New York, 1982, pp. 52–57.

*Primary Examiner*—John W. Rollins
*Assistant Examiner*—L. Eric Crane
*Attorney, Agent, or Firm*—George M. Gould; William H. Epstein; Patricia S. Rocha

[57] ABSTRACT

A process for the isolation of nucleic acids from cell or tissue extracts by precipitating the nucleic acids with a water-soluble ketone, preferably with acetone, optionally in the presence of dimethylformamide or formamide.

6 Claims, 2 Drawing Sheets

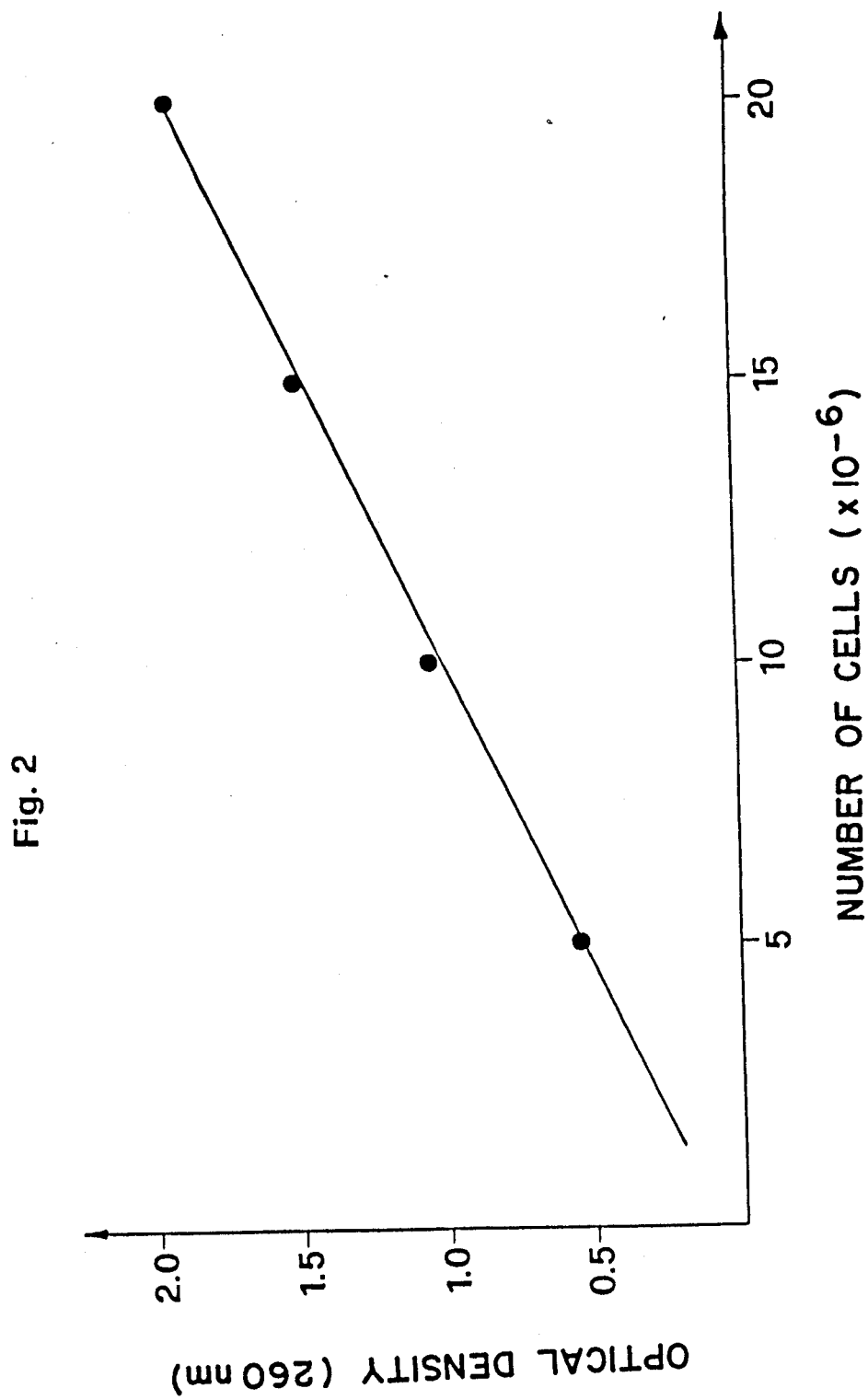

PROCESS FOR ISOLATING NUCLEIC ACIDS

TECHNICAL FIELD

This invention relates to the isolation of RNA or DNA from tissue or cell extracts using water-soluble ketones with or without aprotic polar solvents

BACKGROUND OF THE INVENTION

In the isolation of desoxyribonucleic acids (DNA) or ribonucleic acids (RNA) from biological tissues or cells, the nucleic acids must be separated from the remaining tissue or cell constituents such as proteins, lipids, etc. To this end, a tissue or cell extract is prepared from which the nucleic acids can be separated in a two-phase system (Mainwaring et al., in "Nucleic Acid Biochemistry and Molecular Biology", Blackwell Scientific Publications Oxford (GB), pp. 75–76 [1982]). Two methods are most commonly used which can also be combined (Maniatis et al., in "Molecular Cloning - A Laboratory Manual", Cold Spring Harbor Laboratory, pp. 458–460 [1982]).

In one method a water/phenol two-phase system is used in which proteins and peptides are precipitated or dissolved in the organic phase while nucleic acids remain in the aqueous phase, provided that a specific salt concentration and a neutral pH are maintained. The second method is the chloroform/isoamyl alcohol or chloroform/octanol method in which the nucleic acids also remain in the aqueous phase, while the other, denatured macromolecules are precipitated at the interface between the phases.

It is essential in the isolation of nucleic acids using these two-phase system methods that the aqueous and organic phases be thoroughly intermixed and then separated again. To achieve a rapid phase separation, centrifugation is usually carried out. In the isolation of intact chromosomal DNA care must also be taken to ensure that, upon mixing, the DNA is not cleaved into small fragments by excessive shearing forces.

After the phases are separated, the organic phase is removed and, where required, the aqueous phase is again extracted with an equal volume of phenol, chloroform/isoamyl alcohol or chloroform/octanol. The extraction of the aqueous phase with the organic phase is carried out until the nucleic acids can be precipitated from the aqueous phase in a pure form with alcohol (e.g. ethanol or isopropanol). Of course, the extraction of nucleic acids in this manner requires a large expenditure of time because of the repeated mixing and centrifugation cycles.

SUMMARY OF THE INVENTION

It has now been found that nucleic acids can be isolated from a cell or tissue extract, preferably after treatment with proteases, by simple precipitation with a water-soluble ketone. This ketone is preferably acetone. The precipitated nucleic acids can then be separated from the mixture by filtration or centrifugation. Where required, the thus-isolated nucleic acids can be washed several times with alcohol, preferably with 70% vol/vol ethanol in water. If desired, prior to washing with the alcohol the nucleic acid precipitate can again be dissolved in water or in a buffer solution, e.g., in STET buffer [8% sucrose, 5% Triton TM X-100, 50 mM ethylenediaminetetraacetic acid disodium salt (EDTA) and 50 mM Tris/HCl (pH 8.0)], and reprecipitated with acetone.

The invention accordingly provides a process for the isolation of nucleic acids from an aqueous cell or tissue extract, which process comprises precipitating the nucleic acids with a water-soluble ketone and separating said acids.

BRIEF DESCRIPTION OF THE FIGURES

The following Figures and the Examples below illustrate various embodiments of the present invention, but are not intended to be limiting in any manner:

FIG. 2—DNA from the indicated numbers of cells (mouse monocyte macrophage cell line J774A.1 ATCC No. TIB 67) was isolated in accordance with Example 1, and the amount of DNA obtained (optical density at 260 nm) in each case was plotted.

DESCRIPTION OF THE INVENTION

Figure 1:
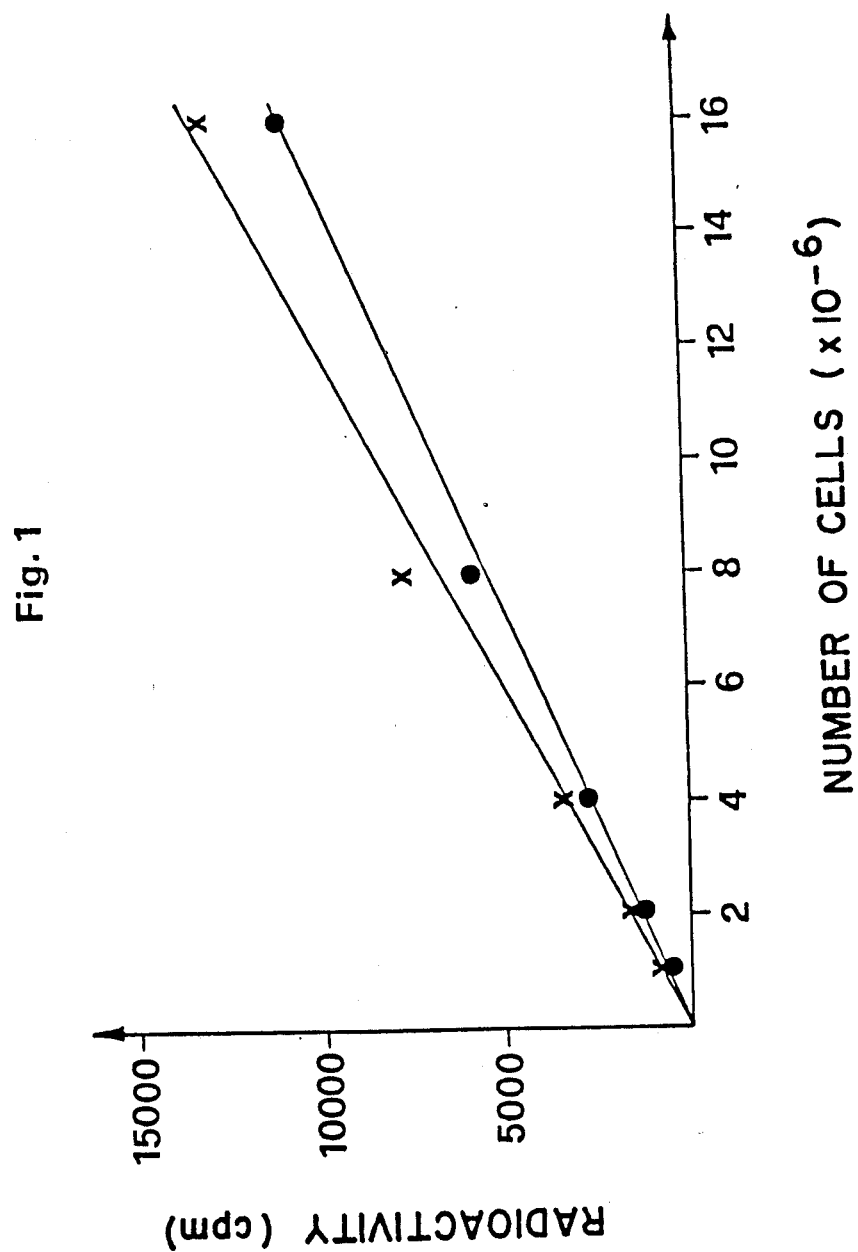
FIG. 1—DNA from the indicated numbers of cells (mouse monocyte macrophage cell line J774A.1, ATCC No. TIB 67), which had previously been labelled during 2 hours with [$^3$H]-thymidine (5 Ci/mmol 1 μCi/ml culture medium, $6 \times 10^5$ cells/ml), was either precipitated directly with ice cold trichloroacetic acid solution on a Whatman TM GF/C filter or isolated in accordance with Example 1. The relative yield was determined by measuring the radioactivity (cpm) of the DNA precipitated on the filter (X) or isolated in accordance with method 1 (●). The DNA from a cell count in the range of $1 \times 10^6$ to $1.6 \times 10^7$ can be isolated virtually quantitatively using the method of the invention.

The process of this invention is suitable for the isolation of nucleic acids, preferably high molecular weight DNA, from a pro- or eukaryotic cell or tissue extract. The high molecular weight DNA can be chromosomal or extrachromosomal DNA. Examples of extrachromosomal DNA are plasmid viral or mitochondrial DNA.

Cell and tissue extracts can be produced by breaking open the cell or tissue structure mechanically chemically or enzymatically. The classical biochemical methods can be used (see, e.g., Mahler et al., Biological Chemistry, 1969, Harper & Row, New York, pp. 389–403). If desired, subcellular fractions such as a cytoplasm fraction or a nucleus fraction can also be used as the starting material.

To avoid DNA degradation by nucleases, nucleases in the extracts can be denatured with detergents (e.g., Triton TM X-100, sodium dodecylsulphate (SDS), etc.), preferably with SDS, and the proteins, including the nucleases, can be degraded by proteases (e.g., pronase, protease K or another nonspecific protease which is active in the presence of detergents; for reaction conditions, see Maniatis et al., supra).

The protease treatment can be carried out at room temperature or at another temperature. It is preferably carried out at a temperature which is optimal for the activity of the protease, i.e. at a temperature of about 37° to 45° C., when protease K or pronase is used. Protease K is also active at a temperature of 65° C. (Maniatis et al., supra, p. 85).

If desired, the cell or tissue extract thus obtained can be diluted, and the nucleic acids can be precipitated by the addition of a water-soluble ketone, preferably acetone. To ensure the precipitation of the nucleic acids, a minimum amount of the water-soluble ketone must be used. On the other hand, the amount of water-soluble ketone should not be so large and the water content should not be so small such that other constituents of the cell or tissue extract, such as peptides, proteins, etc, are precipitated. The optimal amount of water-soluble ketone which is required for the precipitation of the nucleic acids, but not the other constituents of the cell or tissue extract, can be readily determined by a person skilled in the art.

Preferably, the nucleic acids (especially DNA) are precipitated by the addition of an excess of at least 60% aqueous acetone, based on the volume of the cell or tissue extract. The addition of 10 parts by volume of 70% aqueous acetone is especially preferred. For example, one part of a cell or tissue extract containing about 0.6 to 300 μg of DNA in 0.5 to 3 ml of STET buffer can be treated with 10 parts of an at least 60%, preferably a 70%, acetone/water solution (vol/vol). Instead of acetone, an analogous water-soluble ketone such as 2-butanone, 2-pentanone, 3-pentanone or 3-methylcyclopentanone can also be used. However dimethyl ketone or acetone is the preferred ketone.

To increase the solubility of cell constituents which are not nucleic acids, the aqueous acetone solution can, if desired, contain a further organic solvent, provided that the precipitation of the nucleic acids is not prevented by such an addition. For example, the addition of up to 0.1 part by volume, preferably 0.05 part by volume, of dimethylformamide or formamide to the aqueous acetone solution increases the solubility of small peptides. Peptides which are poorly soluble in water are thereby held in solution, and the nucleic acids are precipitated in a purer form. The addition of dimethylformamide or formamide also slows down the rate of precipitation. As a result, the nucleic acids are precipitated in an even purer form when these solvents are added. For the precipitation of nucleic acids from dilute solutions it may be desirable to avoid the addition of dimethylformamide or formamide so that the rate of precipitation of the nucleic acids is not slowed down too greatly.

The precipitation of the nucleic acids takes place spontaneously after the addition of the acetone solution. If desired, the vessel which contains the mixture can be agitated slightly, e.g., by a rocking motion.

The vessel used in the process of the invention should be resistant to the solvent employed, at least for the duration of the process. Vessels of glass, Teflon ™ or polypropylene are preferred.

The precipitated nucleic acid can be filtered off or separated from the solution using other standard methods such as centrifugation and subsequent removal of the supernatant.

Depending on purity requirements, the nucleic acids can be used directly or can be subjected to further purification. For further purification, the nucleic acids can be dissolved again in a buffer solution and reprecipitated as described above or with alcohol, e.g., with ethanol or isopropanol as described by Maniatis et al. (supra, pp. 461–462). The precipitation can be repeated once or several times. Subsequently, the precipitated nucleic acids can be washed with alcohol, preferably with 70% ethanol (vol/vol) in water, and, if desired, once again with absolute alcohol, e.g., ethanol.

If desired, the precipitated nucleic acids can be dried in a vacuum or under a slight stream of nitrogen. If desired, the further purification of the nucleic acids can also be carried out by dialysis (e.g., against 10 mM Tris/HCl (pH 7.8), 100 mM NaCl, 1 mM EDTA).

The process of this invention is preferably carried out at room temperature or in a cooling chamber (e.g., at 4° C.).

DNA isolated using the process of this invention remains stable even in the case of lengthy incubation at room temperature or at 37° C. It can be cleaved specifically by restriction enzymes and is biologically active.

To determine the purity of the nucleic acids obtained, the ratio of the UV absorption at 260 nm and 280 nm can be measured.

EXAMPLES

This invention can be more readily understood by reference to the following, nonlimiting examples.

EXAMPLE 1

$1 \times 10^7$ cells of a B-cell line were lysed in a polypropylene test tube (Falcon 2059, 17×100 mm) by adding 1 ml of lysis buffer (50 mm Tris/HCl (pH 9–10), 100 mM EDTA, 1% SDS). The proteins were digested for 90 minutes at 37° C. by adding 100 μl of a 20 mg/ml pronase solution. Subsequently, 10 ml of solution P consisting of 95 percent by volume 70% acetone in water (vol/vol) and 5 percent by volume dimethylformamide (DMF) were added at room temperature. The mixture was mixed well by rocking the test tube at room temperature for 5 minutes. Initially long DNA filaments formed a small skein.

The DNA was filtered off and washed 3 times with 70% ethanol in water and then twice with absolute ethanol. The DNA was dried with a stream of nitrogen and subsequently dissolved in 1.0 ml of water. Yield: 100 μg, $A_{260}/A_{280}=1.8$. The isolated DNA was stable over several days (agarose gel electrophoresis in accordance with Maniatis et al., supra, pp. 150–161).

EXAMPLE 2

100 ml of an overnight culture of E. coli K 802 (ATCC No. 33526) containing the plasmid pAG60 (Traunecker, Immunol. Methods 3, 55–67 [1985]) were centrifuged at 4000×g for 10 minutes at 4° C., and the cells in the sediment were lysed in accordance with the method of Maniatis et al. (supra, pp. 89–91). The cell lysate (2 ml) was treated with 10 ml of solution P, and the DNA was isolated as in Example 1. Yield: 200 μg, $A_{260}/A_{280}=1.83$. The isolated DNA was stable over several days and could be cleaved with various restriction enzymes.

EXAMPLE 3

The DNA from $1.5 \times 10^7$ cells of a macrophage tumour cell line was precipitated as described in Example 1 using 3 different compositions of solution P.

| | |
|---|---|
| Experiment A: solution P = | 70% acetone in water (vol/vol) |
| Experiment B: solution P = | 95 percent by volume 70% acetone in water (vol/vol) and 5 percent by volume dimethylformamide |
| Experiment C: solution P = | 95 percent by volume 70% acetone in water (vol/vol) and 5 percent by volume formamide. |

Subsequently, the DNA was filtered off and washed three times either with 70% ethanol or with 70% isopropanol. The dried DNA was dissolved in 1 ml of TE buffer (20 mM Tris/HCl (pH 7.6), 2 mM EDTA). It was evident that in all experiments the DNA could be isolated virtually quantitatively and was digestible with restriction enzymes (e.g., with EcoR1). The DNA was stable for at least 18 hours at 4° C., room temperature and 37° C., which indicates that the isolated DNA was free from nucleases.

Many modifications and variations of this invention can be made without departing from its spirit and scope, as will be apparent to those skilled in the art. The specific embodiments described herein are offered by way of example only, and the invention is limited only by the terms of the appended claims.

What is claimed is:

1. A process for isolating nucleic acids from a bacterial cell lysate, which process comprises:
   (a) preparing a bacterial cell lysate;
   (b) centrifuging the lysate to sediment cellular debris and to produce a clear supernatant;
   (c) treating the clear supernatant with an excess of an aqueous solution containing at least 60% by volume of a water-soluble ketone selected from the group consisting of acetone, 2-butanone, 2-pentanone, 3-pentanone and 3-methylcyclopentanone, to produce a mixture containing precipitated nucleic acids; and
   (d) separating the precipitated nucleic acids from the mixture, thereby isolating the nucleic acids from the extract.

2. The process of claim 1 in which the nucleic acids are precipitated with acetone.

3. The process of claim 1 in which the nucleic acids are DNA.

4. The process of claim 2 in which one volume of the clear supernatant is treated with 10 volumes of 70% by volume aqueous acetone.

5. The process of claim 2 in which the aqueous acetone solution contains 0.05 to 0.1 parts by volume of dimethylformamide or formamide.

6. The process of claim 1 in which the bacterial cell is an *E. coli* bacterium.

* * * * *